US012161465B2

United States Patent
Kim et al.

(10) Patent No.: US 12,161,465 B2
(45) Date of Patent: Dec. 10, 2024

(54) BIOSENSOR AND MANUFACTURING METHOD THEREFOR

(71) Applicants: Samsung Electronics Co., Ltd., Suwon-si (KR); INSTITUTE FOR RESEARCH & INDUSTRY COOPERATION, PUSAN NATIONAL UNIVERSITY, Busan (KR)

(72) Inventors: Kwang-bok Kim, Incheon (KR); Yoon-Bo Shim, Busan (KR); Han-gyol Park, Seoul (KR); Youn-joo Song, Seoul (KR); Seong-je Cho, Suwon-si (KR); Chul-ho Cho, Yongin-si (KR); Dong-Min Kim, Busan (KR)

(73) Assignees: Samsung Electronics Co., Ltd., Suwon-si (KR); INSTITUTE FOR RESEARCH & INDUSTRY COOPERATION, PUSAN NATIONAL UNIVERSITY, Busan (KR)

( * ) Notice: Subject to any disclaimer, the term of this patent is extended or adjusted under 35 U.S.C. 154(b) by 1739 days.

(21) Appl. No.: 16/316,194

(22) PCT Filed: Dec. 29, 2016

(86) PCT No.: PCT/KR2016/015461
§ 371 (c)(1),
(2) Date: Jan. 8, 2019

(87) PCT Pub. No.: WO2018/012692
PCT Pub. Date: Jan. 18, 2018

(65) Prior Publication Data
US 2021/0282681 A1 Sep. 16, 2021

(30) Foreign Application Priority Data

Jul. 11, 2016 (KR) .................. 10-2016-0087701
Sep. 9, 2016 (KR) .................. 10-2016-0116126

(51) Int. Cl.
*A61B 5/1486* (2006.01)
*A61B 5/145* (2006.01)
(Continued)

(52) U.S. Cl.
CPC ........ *A61B 5/14865* (2013.01); *C08G 61/126* (2013.01); *C12Q 1/006* (2013.01);
(Continued)

(58) Field of Classification Search
None
See application file for complete search history.

(56) References Cited

U.S. PATENT DOCUMENTS

2009/0008248 A1   1/2009   Shimomura et al.
2016/0054252 A1   2/2016   Cho et al.

FOREIGN PATENT DOCUMENTS

JP        5026873 B2       9/2012
KR   10-2008-0104495 A   12/2008
(Continued)

OTHER PUBLICATIONS

M.M. Rahman, et al., "A lactate biosensor based on lactate dehydrogenase/nictotinamide adenine dinucleotide (oxidized form) immobilized on a conducting polymer/multiwall carbon nanotube composite film", Analytical Biochemistry, 384(1): p. 159-165, Jan. 2009.*

(Continued)

*Primary Examiner* — J. Christopher Ball
(74) *Attorney, Agent, or Firm* — Jefferson IP Law, LLP

(57) ABSTRACT

Disclosed is a biosensor. The biosensor comprises: an electrode; and a polymer structure disposed on the electrode and
(Continued)

formed of poly-5,2':5',2"-terthiophene-3'-carboxylic acid (pTTCA), wherein an enzyme is present in a state of covalently binding with pTTCA inside the polymer structure.

5 Claims, 15 Drawing Sheets

(51) Int. Cl.
*C08G 61/12* (2006.01)
*C12Q 1/00* (2006.01)
*C25B 3/29* (2021.01)
*G01N 27/327* (2006.01)

(52) U.S. Cl.
CPC ............ *C25B 3/29* (2021.01); *G01N 27/3271* (2013.01); *G01N 27/3275* (2013.01); *A61B 5/14532* (2013.01); *C08G 2261/11* (2013.01); *C08G 2261/228* (2013.01); *C08G 2261/3223* (2013.01); *C08G 2261/94* (2013.01)

(56) References Cited

FOREIGN PATENT DOCUMENTS

| | | | |
|---|---|---|---|
| KR | 10-2013-0087239 A | 8/2013 | |
| KR | 10-1370724 B1 | 3/2014 | |
| KR | 10-2014-0078644 A | 6/2014 | |
| KR | 10-2014-0085228 A | 7/2014 | |
| KR | 10-1494542 B1 | 2/2015 | |
| KR | 10-2016-0023483 A | 3/2016 | |
| WO | 2008/146966 A1 | 12/2008 | |
| WO | 2013/058879 A2 | 4/2013 | |
| WO | 2014/096407 A1 | 6/2014 | |

OTHER PUBLICATIONS

A. El-Laboudi, et al., "Use of Microneedle Array Devices for Continuous Glucose Monitoring: A Review", Diabetes Technology & Therapeutics, 15(1): p. 101-115, Jan. 2013.*
W.C.A. Koh, et al. "A cytochrome c modified-conducting polymer microelectrode for monitoring in vivo changes in nitric oxide" Biosensor & Bioelectronics, 23(9): p. 1374-1381, Apr. 2008.*
A.A. Abdelwahab, et al. "A selective nitric oxide nanocomposite biosensor based on direct electron transfer of microperoxidase: Removal of interferences by co-immobilized enzymes", Biosensors & Bioelectronics, 26(3): p. 1080-1086, Nov. 2010.*
M.A. Rahman, et al. "The biosensor based on the pyruvate oxidase modified conducting polymer for phosphate ion determinations", Biosensor & Bioelectronics, 21(7): p. 1116-1124, Jan. 2006.*
M.A. Rahman, et al. "A performance comparison of choline biosensors: anodic or cathodic detections of H2O2 generated by enzyme immobilized on a conducting polymer", Biosensors & Bioelectronics, 19(12): p. 1565-1571, Jul. 2004.*
M.A. Rahman, et al. "Xanthine Sensors Based on Anodic and Cathodic Detection of Enzymatically Generated Hydrogen Peroxide", Electroanalysis, 19(6): p. 631-637, Mar. 2007.*
M.J.A. Shiddiky, et al. "Analysis of polymerase chain reaction amplifications through phosphate detection using an enzyme-based microbiosensor in a microfluidic device", Electrophoresis, 27(14): p. 2951-2959, Jul. 2006.*
H.-J. Kim, et al. "Characterization of Protien-Attached Conducting Polymer Monolayer", Langmuir, 24(3): p. 1087-1093, Feb. 2008.*
D.-M. Kim, et al., "Disposable all-soild-state pH and glucose sensors based on conductive polymer covered hierarchical AuZn oxide", Biosensor & Bioelectronics, 79: p. 165-172, May 2016.*
Korean Office Action with English translation dated Nov. 24, 2020; Korean Appln. No. 10-2016-0116126.
Aminur Rahman et al., "The potential use of hydrazine as an alternative to peroxidase in a biosensor: comparison between hydrazine and HRP-based glucose sensors", Department of Chemistry and Center for Innovative Bio-Physio Sensor Technology, Pusan National University, Jul. 29, 2004, Busan, South Korea.

* cited by examiner

BIOSENSOR AND MANUFACTURING METHOD THEREFOR

FIELD OF THE INVENTION

Devices and methods consistent with what is disclosed herein relate to a biosensor and a manufacturing method thereof, and more particularly, to a biosensor capable of ensuing reproducibility even in continuous measurement, and a manufacturing method thereof.

DESCRIPTION OF THE RELATED ART

Quantitative determination of an analyte in biological fluids is useful for diagnosis and treatment of physiological abnormalities. For example, in diagnosing and preventing diabetes, the amount of glucose (blood glucose) needs to be periodically checked.

Conventionally, a biosensor using an electrochemical method has been mainly used. An electrochemical biosensor is an apparatus that measures the amount of a substance to be measured by detecting an electrochemical signal through an enzyme reaction with an analyte using an enzyme electrode having an enzyme fixed to an electrode.

A biosensor can measure the amount of a substance to be measured in various ways. Among the methods in which blood sampling is required, blood glucose measurement values can be changed according to proficiency of a blood sampling method. Also, it is impossible to completely detect changes in the concentration of a substance to be measured only with a few intermittent measurements.

Recently, a device capable of accurately monitoring the concentration of a substance to be measured without blood collection has been developed. Typically, a complete implantable type in which the biosensor itself is completely implanted into the body, and a minimally invasive type in which a needle-shaped sensor is inserted into subcutaneous tissue have been used.

Meanwhile, since the minimally invasive type biosensor is inserted into the subcutaneous tissue instead of the blood vessel, direct contact with the blood can be avoided. Therefore, the biosensor can be operated for several days by using a biocompatible material. There is an advantage in that the biosensor could be inserted into a patient without surgery by a specialist.

When glucose is measured in body fluids with such a minimally invasive biosensor, the glucose level is inaccurately measured due to an interfering substance such as chloride ion (Cl—) present in body fluids. In addition, since the biosensor is continuously inserted into the skin, the enzyme is released from the electrode into the body fluids due to long-term use, and thus an inaccurate level is measured.

Therefore, it is required to develop a biosensor capable of exhibiting excellent reproducibility in continuous measurement thanks to the enzyme fixed to the electrode while the influence of the interfering substance is minimized.

The present disclosure is designed to solve the above-mentioned problems, and an object of the present disclosure is to provide a biosensor capable of ensuring reproducibility even in continuous measurement, and a method of manufacturing the biosensor.

SUMMARY

According to an exemplary embodiment, there is provided a biosensor including an electrode, and a polymer structure disposed on the electrode and formed of poly-5,2': 5',2"-terthiophene-3'-carboxylic acid (pTTCA), wherein an enzyme is in covalent bonding with pTTCA in the polymer structure.

The biosensor may further include a gold-zinc alloy oxide layer (AuZn oxide layer) disposed between the electrode and the polymer structure.

The enzyme may have an amine group, and wherein the amine group of the enzyme and a carboxyl group of pTTCA form the covalent bonding.

The enzyme may be selected from a group consisting of glucose oxidase, glucose dehydrogenase, hexokinase, glutamic oxaloacetic transaminase, and glutamine pyruvic transaminase.

The biosensor may further include a supporting body disposed under the electrode, wherein the electrode has a needle shape disposed in a vertical direction based on the supporting body.

According to an exemplary embodiment, there is provided a method for manufacturing a biosensor, the method including generating monomers formed by covalent boding between 5,2':5',2"-terthiophene-3'-carboxylic acid (TTCA) and an enzyme, and polymerizing the monomers on an electrode and depositing a polymer layer on the electrode.

The method may further include coating an electrode surface with a gold-zinc alloy oxide layer (AuZn oxide layer), wherein the depositing of the polymer layer on the electrode comprises polymerizing the monomers on an electrode coated with the gold-zinc alloy oxide layer.

The enzyme may include an amine group, and wherein the generating of the monomers comprises using 1-Ethyl-3-[3-(dimethylamino)propyl]carbodiimide hydrochloride (EDC) and N-hydroxysuccinimide (NHS) and activating a carboxyl group of the TTCA to form covalent bonding between the carboxyl group of the TTCA and the amine group of the enzyme.

The enzyme may be selected from a group consisting of glucose oxidase, glucose dehydrogenase, hexokinase, glutamic oxaloacetic transaminase, and glutamine pyruvic transaminase.

The depositing of the polymer layer on the electrode may include immersing the electrode in a solution containing the monomers, and applying a voltage to the electrode to polymerize the monomers on the electrode by electropolymerization.

DETAILED DESCRIPTION OF EXEMPLARY EMBODIMENTS

The present disclosure is not limited to an embodiment disclosed below and may be implemented in various forms and the scope of the present disclosure is not limited to the following embodiments. In addition, all changes or modifications derived from the meaning and scope of the claims and their equivalents should be construed as being included within the scope of the present disclosure. In the following description, the configuration which is publicly known but irrelevant to the gist of the present disclosure could be omitted. In addition, the attached drawings are not drawn to scale to facilitate understanding of the present disclosure, but the dimensions of some of the components may be exaggerated.

Figure 1:
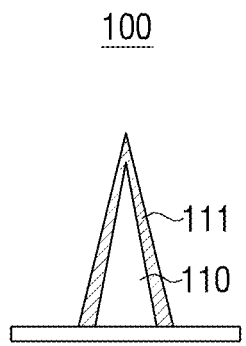
FIG. 1 is a view illustrating a biosensor according to an embodiment of the present disclosure.

FIG. 1 is a view to explain a biosensor 100 according to an embodiment of the present disclosure.

The biosensor 100 may be a device capable of measuring a target substance by an electrochemical method using a biological substance having a specific recognition ability for a substance to be analyzed, for example, an enzyme. Although the term biosensor is used, it can be referred to variously, for example, as a sensor, a measuring device, a measuring instrument, etc. Depending on the subject to be measured, various names such as a hydrogen peroxide sensor, a glucose sensor, and a blood glucose sensor can be used.

Electron migration may occur due to biochemical oxidation-reduction reaction occurring on the electrode surface of the biosensor 100 and the concentration of the substance in the sample may be measured by monitoring the current generated by the movement of electrons.

The biosensor 100 may include a working electrode and a counter electrode (counter or counter/reference electrode). Alternatively, the biosensor 100 may include a working electrode, a counter electrode, and a separate reference electrode.

The operation electrode may be an electrode to which an enzyme is fixed, and can be referred to as an enzyme-fixed electrode or an enzyme electrode. FIG. 1 is a cross-sectional view illustrating a structure of an electrode to which an enzyme is fixed among various electrodes of the biosensor 100.

Referring to FIG. 1, the biosensor 100 may include an electrode 110 on which a polymer-structure body 111 is deposited.

Referring to FIG. 1, when the biosensor 100 is implemented as a continuous blood glucose measurement sensor, the electrode is shown as having a needle shape so as to be infiltrated into the skin. However, the shape is not necessarily limited to such a shape, and could have various shapes.

The electrode 110 may be made of a metal or an alloy such as carbon, gold, platinum, silver, copper, or palladium.

The polymer structure 111 may be disposed on the electrode 110 and contain an enzyme therein. Specifically, in the polymer structure 111, an enzyme may be present inside the polymer structure 111 with a covalent bond (polymer-enzyme) between the polymer and the enzyme.

The polymer structure 111 may be obtained by polymerizing a monomer (TTCA-enzyme) formed by covalently bonding 5,2':5',2"-terthiophene-3'-carboxylic acid (5,2':5,2"-terthiophene-'-carboxylic acid) (hereinafter referred to as TTCA) with an enzyme. The polymer structure 111 may be formed of poly-5,2':5,2"-terthiophene-3'-carboxylic acid) (hereinafter referred to as pTTCA), and the enzyme may be covalently bound to the pTTCA (pTTCA-enzyme) in the polymer structure 111.

The enzyme may include an amine group, and a covalent bond may be formed between the amine group of the enzyme and the carboxyl group of the pTTCA.

Figure 2:
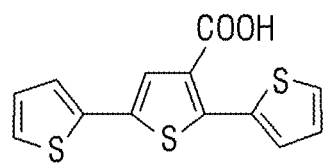
FIG. 2 is a view showing the chemical structure of 5,2': 5',2"-terthiophene-3'-carboxylic acid (TTCA)
Figure 3:
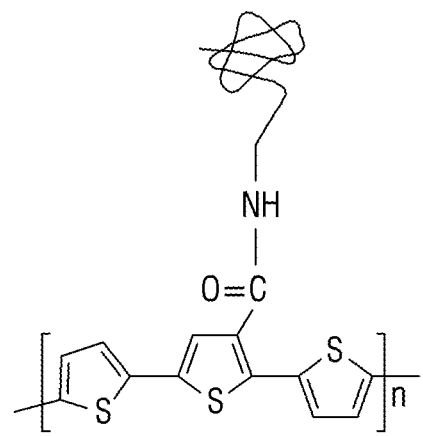
FIG. 3 is a view showing a monomer formed by covalent bonding of TTCA and enzyme.

TTCA may be a polymer monomer having excellent physical, chemical, mechanical and electrical properties. FIG. 2 illustrates the structure thereof, and FIG. 3 illustrates the monomer formed by covalent bonding of TTCA and an enzyme. The monomer formed by covalent bonding of TTCA and enzyme may have electrical conductivity and may be polymerized through electropolymerization.

As shown in FIG. 3, when an enzyme polymerizes a covalently bonded monomer, the enzyme can be strongly fixed in the polymer structure 111 by a covalent bond. Therefore, even in the long-term use of the biosensor 100, the enzyme can be prevented from being deviated to the outside. Further, the polymer and the enzyme can be simultaneously fixed to the electrode.

In addition to TTCA, monomers of a conducting polymer having a carboxyl group may be used to form the polymer structure 111. For example, terthiophene benzoic acid (TTBA), di-thienylpyrrole benzoic acid (DTPBA) and the like may be used. When TTBA is used, the polymer structure 111 may be a polymerized TTBA-enzyme monomer, and the structure thereof may be such that the enzyme is covalently bonded to the poly-TTAA within the structure formed of poly-TTABA. When DTPBA is used, the polymer structure 111 may be a polymerized DTPBA-enzyme monomer, and the structure thereof may be such that the enzyme is covalently bonded to poly-DTPBA in the structure formed of poly-DTPBA.

The enzyme may be selected from various enzymes having an amine group according to the substance to be detected. For example, the enzyme may be selected from a group consisting of glucose oxidase (GOx), glucose dehydrogenase (GDH), hexokinase, glutamic-oxaloacetic transaminase, and glutamic-pyruvic transaminase, but the present disclosure is not limited thereto.

For example, when the substance to be detected is glucose, when glucose oxidase fixed on the polymer structure 111 reacts with glucose, it may be oxidized to gluconic acid. When glucose is oxidized, glucose can be quantified by measuring the current due to the transfer of electrons generated when oxygen or oxidized medium is converted to hydrogen peroxide or reduced medium and then oxidized to be returned to the original oxidized form.

According to another embodiment of the present disclosure, the biosensor 110 may further include an alloy oxide layer disposed between the electrode 110 and the polymer structure 111. The alloy oxide layer may be formed of a metal selected from the group consisting of copper, cobalt, gold, platinum, and zinc. As a specific example, the alloy oxide layer disposed between the electrode 110 and the polymer structure 111 may be a gold-zinc alloy oxide layer (AuZn oxide layer).

In order to form an alloy oxide layer on the surface of the electrode 110, electrodeposition may be performed in a solution containing two or more different metal ions, and the electrodeposited metal layer may be dipped in PBS and oxidized using amperometry.

When the alloy oxide layer is applied to the surface of the electrode 110, the surface area of the electrode may be increased, so that the sensitivity may be improved. In addition, the alloy oxide layer may exhibit excellent electrochemical catalytic properties for hydrogen peroxide ($H_2O_2$) generated by the reaction of glucose and glucose oxidase during glucose measurement. In addition, it is possible to prevent contamination of the electrode surface by impurities, thereby improving the sensitivity of the biosensor. For example, in the case of measuring glucose in the blood, there is a problem in that the measurement sensitivity of glucose is lowered when ions such as Cl—, etc. are adsorbed on the surface of the electrode. An alloy oxide layer of the electrode surface may be prevented impurities from being attached.

Figure 4:
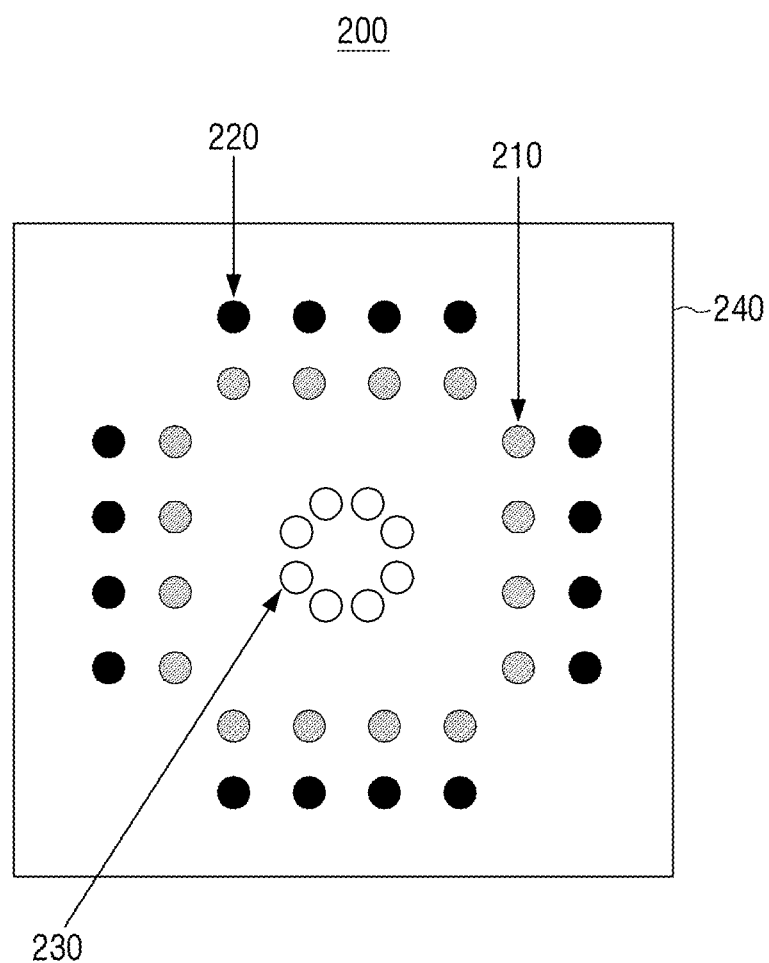
FIG. 4 is a view to explain a biosensor according to another embodiment of the present disclosure.

FIG. 4 is a view illustrating a biosensor having an electrode to which the above-described enzyme is fixed (operation electrode) together with other electrodes according to an embodiment of the present disclosure. FIG. 4 is a conceptual plane view illustrating the arrangement of electrodes of a biosensor.

Referring to FIG. 4, a biosensor 200 may include a plurality of operation electrodes 210, a plurality of counter electrodes 220, a plurality of reference electrodes 230, and a support body 240 which supports each of the electrodes.

Referring to FIG. 1, the operation electrode 210 may be an electrode to which an enzyme is fixed.

The counter electrode 220 may have an opposite polarity to the operation electrode and may be formed of an electrode material having high electrical conductivity since it is a current path between the electrodes. Each of the plurality of counter electrodes 220 may be made of a metal or an alloy such as carbon, gold, platinum, silver, copper, or palladium as the operation electrode.

The reference electrode 230 may apply a constant potential to the operation electrode, and the current may not flow toward the electrode due to the high impedance. The reference electrode 230 may be, for example, a standard hydrogen electrode (SHE), a calomel ($Hg/Hg_2Cl_2$) electrode, or a silver-silver chloride (Ag/AgCl) electrode. Since reference electrodes 230 have a relatively constant potential difference, a constant electrode potential may be applied.

The biosensor 200 may measure the blood glucose level. In this case, the operation electrode 210, the counter electrode 220, and the reference electrode 230 may have a needle shape so that the biosensor 220 may be inserted into the skin.

Electrodes in a needle shape may be disposed in a vertical direction based on the supporting body 240. To be specific, when the biosensor 200 needs to be attached to skin to measure blood glucose, the supporting body 240 may be formed of a flexible material such as rubber, so that electrodes in a needle shape may be inserted into the skin. The supporting body 240 may be in a band type to be attached to the body so that the biosensor 200 can be easily attached to the body.

Figure 5:
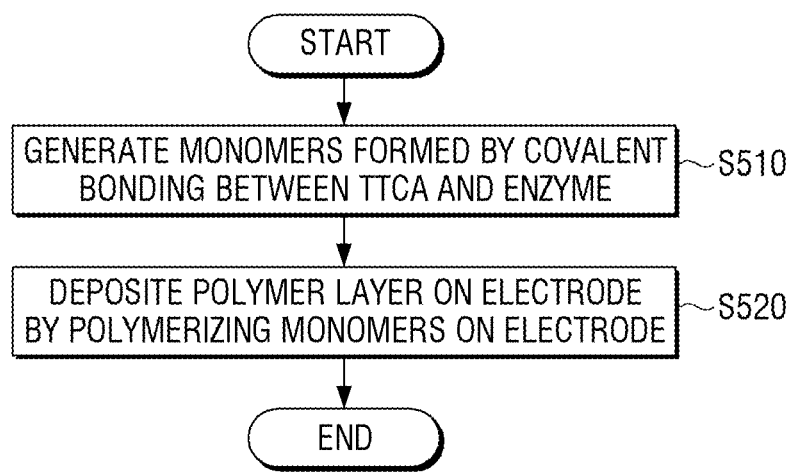
FIG. 5 is a view to explain a manufacturing method of a biosensor according to an embodiment of the present disclosure.

FIG. 5 is a flowchart to explain a method for manufacturing a biosensor according to an embodiment of the present disclosure.

Referring to FIG. 5, monomers formed by covalent bonding between 5,2': 5', 2"-terthiophene-3'-carboxylic acid (TTCA) and an enzyme may be generated at step S510.

Specifically, the carboxyl group of TTCA may be activated by using EDC (1-Ethyl-3-[3-(dimethylamino)propyl] carbodiimide hydrochloride) and NHS (N-hydroxysuccinimide), and a covalent bond between the carboxyl group of TTCA and the amine group of the enzyme may be formed.

In addition to TTCA, conductive monomers having a carboxyl group such as terthiophene benzoic acid (TTBA), di-thienylpyrrol benzoic acid (DTPBA) and the like may be used. When TTBA is used, EDC and NHS may be used to activate the carboxyl group of TTBA to form a covalent bond between the carboxyl group of TTBA and the amine group of the enzyme. When DTPBA is used, EDC and NHS may be used to activate the carboxyl group of DTPBA to form a covalent bond between the carboxyl group of DTPBA and the amine group of the enzyme.

Examples of enzymes containing an amine group that can be used herein may include glucose oxidase, glucose dehydrogenase, hexokinase, glutamic oxaloacetic transaminase, and glutamine pyruvic transaminase.

The formed monomers may be polymerized on the electrode to deposit a polymer layer on the electrode at step S520.

The formed monomers may have conductivity and can be polymerized through electropolymerization.

Specifically, the electrodes may be immersed in a solution containing monomers, and voltages may be applied to the electrodes through potential scanning to polymerize the monomers on the electrodes. In particular, since a plurality of electrodes are present in the biosensor as described above, the polymer layer may be deposited only on the electrode to which voltage is applied by selectively applying a voltage only to the electrode to be the operation electrode.

In this case, the polymer layer may be deposited by a cyclic voltammetry (CV) method.

According to the above-described method, the polymer layer may be easily and selectively deposited only on the electrode to be the operation electrode in the electrode array including the plurality of electrodes, and the polymer layer may be formed on the electrode at once without multiple processes. Therefore, it is advantageous in that the process can be simplified.

On the other hand, before the polymer layer is deposited, the electrode may be coated with an alloy oxide. This is to prevent contamination of the electrode surface from impurities other than the measurement target substance and to widen the surface area in order to increase the measurement sensitivity.

Specifically, an electrode may be immersed in a solution in which a metal salt is dissolved, and a voltage may be applied to form an alloy layer on the surface of the electrode. In this case, a normal pulse voltammetry (NPV) may be used. Examples of metals that can be used may include copper, cobalt, gold, platinum, and zinc. As a specific example, an alloy layer of gold and zinc (AuZn layer) may be formed on the electrode surface by a pulse voltage/current method.

After the alloy layer is formed, the alloy layer may be oxidized at a constant voltage using amperometry by immersing the electrode in a buffer solution such as a PBS solution. The oxidized alloy layer may have a wide surface area structure, and thus the measurement sensitivity may be improved.

The above-described biosensor may reduce disturbance to Cl— ions and enhance glucose detection sensitivity by employing a metal alloy oxide layer and a pTTCA-enzyme layer. Moreover, it is very stable even in repeated measurement, and continuous measurement is possible even in the skin.

Hereinafter, the present disclosure will be described through specific example embodiments and experimental example. The following examples and experimental examples are only for the purpose of helping understanding the present disclosure, but the present disclosure is not limited by the following examples and experimental examples.

Figure 6:
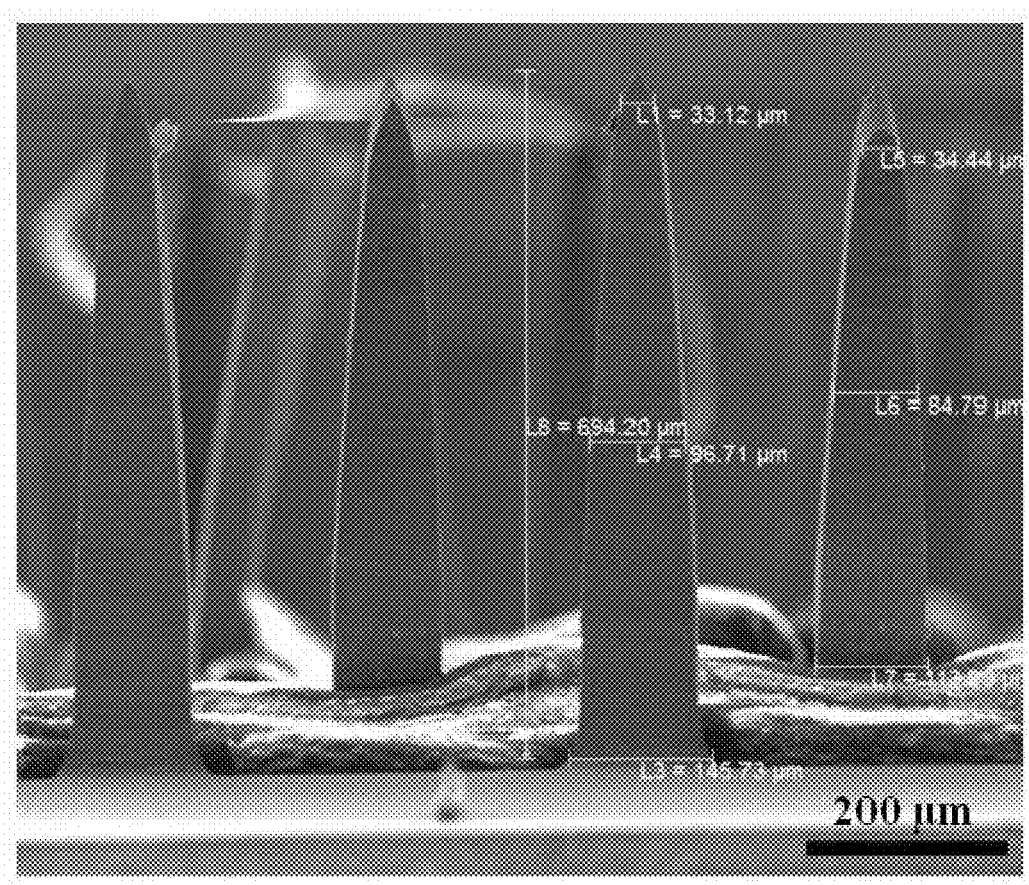
FIG. 6 is a scanning electron microscope (SEM) image of a micro needle electrode of a biosensor according to an embodiment of the present disclosure.

<Example Embodiment 1> Manufacturing of a Blood Glucose Sensor Based on a Micro Array Needle Electrode The manufacturing process will be described with reference to FIGS. 6 to 7. First, a micro needle array electrode as shown in the SEM photograph of FIG. 6 is prepared. As shown in FIG. 6, the length and width of needle-shaped electrodes may be very small, about 700 μm and 100 μm, so that even when it is infiltrated into the skin, there may be little pain. Therefore, the pain may be less and, in addition, the problem of secondary infection can be overcome as compared with the method of collecting blood with a lancet.

Figure 7:
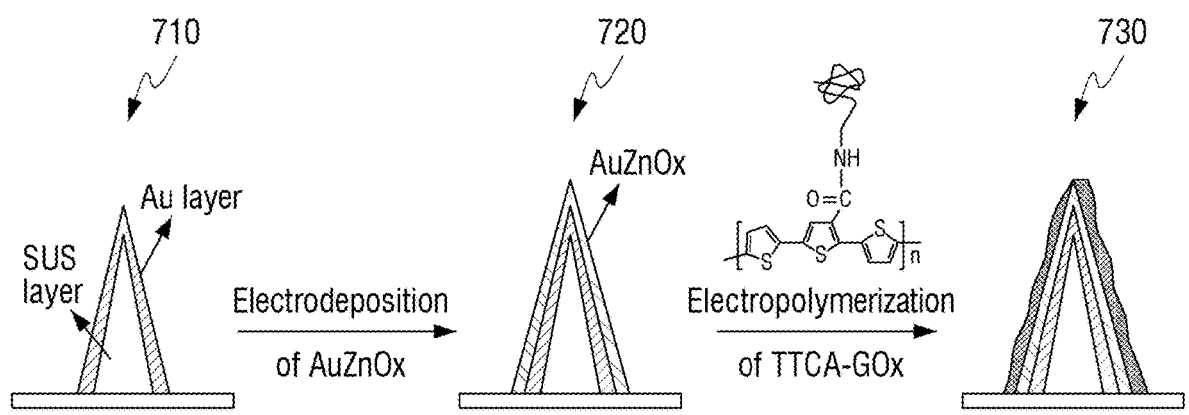
FIG. 7 is a view to explain a manufacturing process of a biosensor according to an embodiment of the present disclosure.

The microneedles may be made of stainless use steel (SUS) and plated with gold (Au) (see 710 in FIG. 7). To form a gold-zinc alloy oxide layer (AuZn oxide layer) on the micro needle array electrode (SUS/AU), a precursor solution in which 30 mM of each of gold (III) chloride trihydrate and zinc chloride is dissolved in distilled water may be prepared. The solution is scanned from 0 to −1.0 V at a scan rate of 200 mV/s using a normal pulse voltammetry (NPV) to form a gold-zinc alloy layer (AuZn layer) and dipping the gold-zinc alloy layer (AuZn layer) in the solution of 0.1 M (PBS, pH 7.4) and oxidize at 1.5 V for 200 seconds using amperometry. Then, it is sequentially washed with ethanol and distilled water, and dried with a cold wind to generate a SUS/Au/AuZnOx electrode (see 720 in FIG. 7).

A mixed solution of conductive polymer monomer (TTCA) and glucose oxidase (GOx) is prepared as follows.
1) Dissolve 1 mM TTCA monomer in acetonitrile/0.1 M TBAP.
2) Prepare a solution of glucose oxidase (GOx) 12 mg/mL and 10 mM EDC/NHS dissolved in distilled water and reacted at room temperature for 4 hrs.
3) The two solutions are mixed to make a final concentration of 0.5 mM TTCA, and 6 mg/mL GOx and reacted at room temperature for 2 hr to form a covalent bond between the carboxyl group of TTCA and the amine group of GOx.

The SUS/Au/AuZnOx electrode may be placed in the mixed solution prepared in step 3), and the conductive polymer-enzyme layer may be formed by the circulating current and voltage method. That is, the polymer and the enzyme may be simultaneously deposited. Specifically, the electro-polymerization conditions of the conductive polymer-enzyme layer may be in a scanning range of 0.0 to 1.7 V, at a scanning speed of 100 mV/s, and at a scanning frequency of 5 times. The scanning is performed 10 cycles until a stable cyclic voltammetric curve is obtained in 0.1 M PBS solution (pH 7.4). Then, the electrode having the polymer-enzyme layer deposited thereon is washed with a mixed solvent of acetonitrile/tertiary distilled water (1:1) and distilled water, followed by drying in a cold wind. The electrode on which the conductive polymer-enzyme layer is formed is dipped once in 0.7% NaOH solution, coated with Nafion polymer film, and dried in CaCl 2 atmosphere for 4 hours to manufacture a glucose sensor (see 730 in FIG. 7).

<Experimental Example 1> Electrochemical Properties of a Glucose Sensor

Figure 8A:
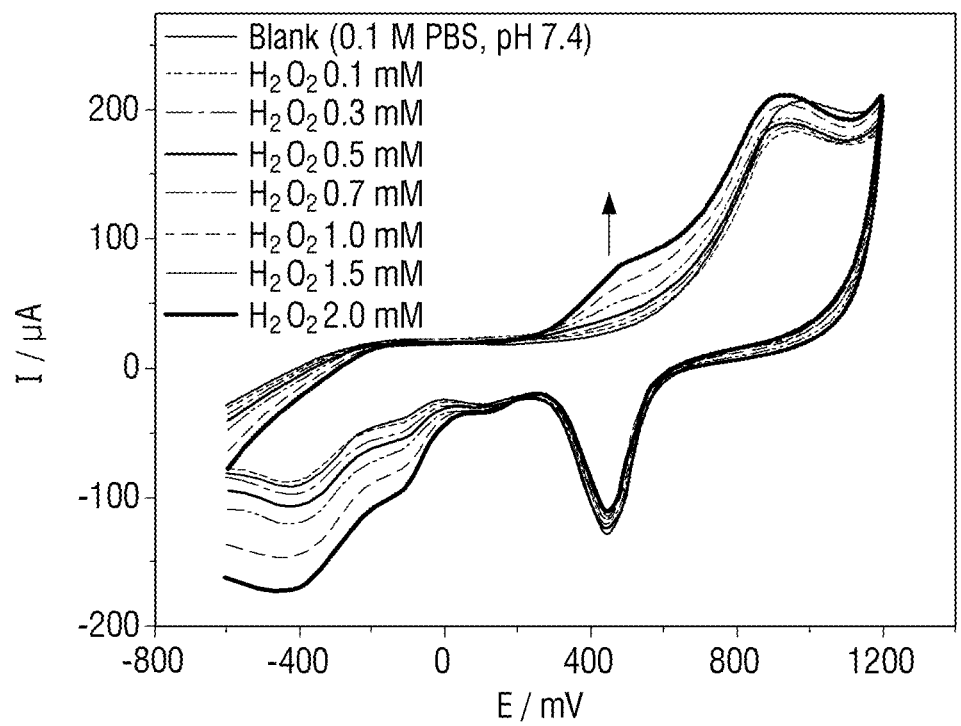
FIGS. 8A and 8B are cyclic voltage and current curves for concentration changes in the measurement of (A) $H_2O_2$ and (B) glucose using a polymer-enzyme electrode according to an embodiment of the present disclosure.
Figure 8B:
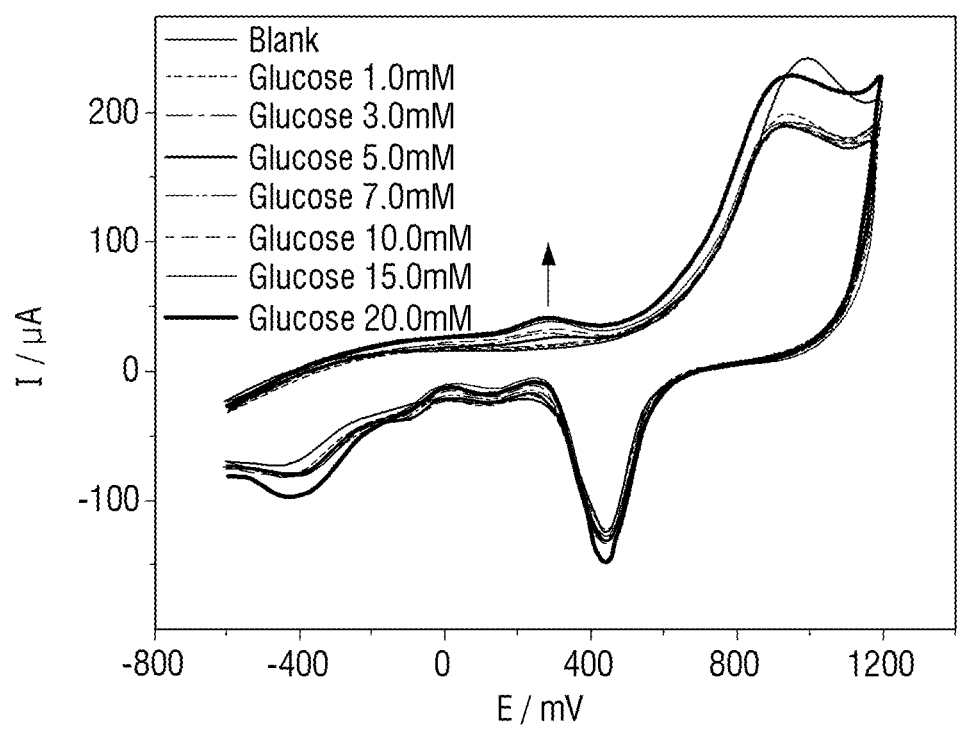

The principle of detecting glucose by a glucose sensor is to indirectly quantify glucose concentration by measuring the current generated by the oxidation of $H_2O_2$ generated through the reaction of GOx with glucose by the Au/AuZnOx layer. Therefore, the reactivity of the electrode prepared in Example 1 to $H_2O_2$ concentration is examined. FIG. 8A is a cyclic voltage-current curve according to $H_2O_2$ concentration using an electrode on which a polymer-enzyme layer (pTTCA-GOx) fabricated according to Example 1 is formed. The concentration of $H_2O_2$ is 0.1, 0.3, 0.5, 0.7, 1.0, 1.5 and 2.0 mM in 0.1 M PBS (pH 7.4) solution. As the $H_2O_2$ concentration increases, the $H_2O_2$ oxidation current increased at about 400 mV. FIG. 8B is a cyclic voltammetric curve according to glucose concentration using an electrode on which a polymer-enzyme layer (pTTCA-GOx) fabricated according to Example 1 is formed. Glucose concentrations may be 1.0, 3.0, 5.0, 7.0, 10.0, 15.0 and 20.0 mM. The oxidation current by glucose is observed to increase at about 350 mV. This means that as the concentration of glucose increases, the concentration of $H_2O_2$, which is a reaction product, increases proportionally.

Figure 9:
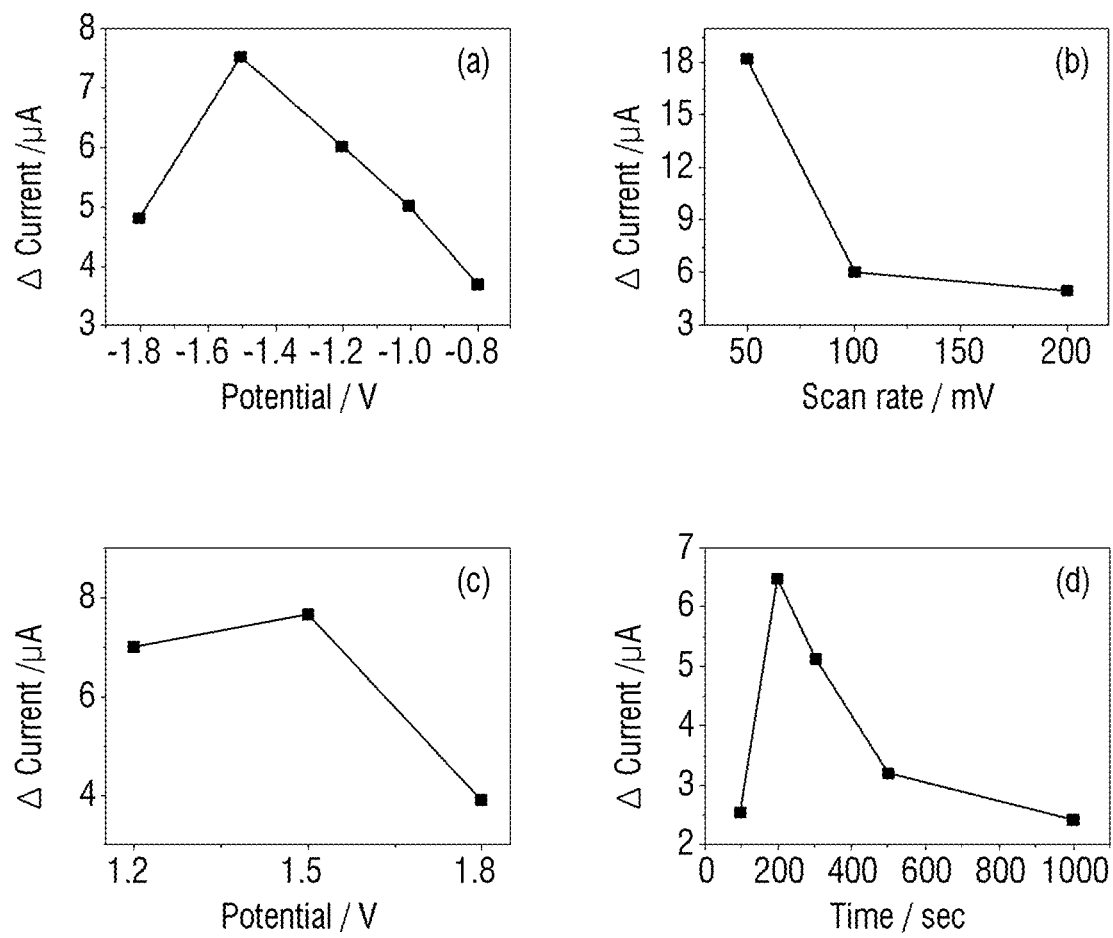
FIG. 9 shows experimental results of the optimization conditions for forming and oxidizing an AuZnOx layer, specifically, experimental results of the optimization conditions for voltage (a), scanning speed (b), AuZn oxidation potential (c), and oxidation time (d) for forming an AuZn layer.

<Experimental Example 2> Identification of Optimization Conditions for Manufacturing a Blood Glucose Sensor Optimization experiments (electrochemical electrodeposition voltage, scanning speed, oxidation potential, and electrodeposition time) for increasing the sensitivity of glucose by reducing the influence of Cl— by increasing the surface area of the metal electrode (SUS/Au) and forming an oxidation layer (see FIG. 9). The concentration of glucose used in this experiment may be 10 mM. Electrodeposition is performed at −0.8, −1.0, −1.2, −1.5, and −1.8 V, respectively, as the optimum experiment, for the electrodeposition voltage of AuZn layer on SUS/Au using normal pulse voltammetry (NPV). The oxidation current of glucose increased from −0.8 V to −1.5 V, but the oxidation current decreased after −1.5 V (see FIG. 9 (*a*)). Therefore, the electrodeposition voltage of AuZn is optimized at −1.5 V. With respect to the scanning speed at the time of electrodeposition of AuZn, the largest glucose oxidation current value is shown at 50 mV/s (see FIG. 9 (b)). As a result of the optimization experiment for the formation of the AuZn oxide film using the time zone current method, the oxidation current is greatest when the oxidation voltage is 1.5 V (see FIG. 9C), the oxidation time is 200 seconds (see FIG. 9D).

Figure 10:
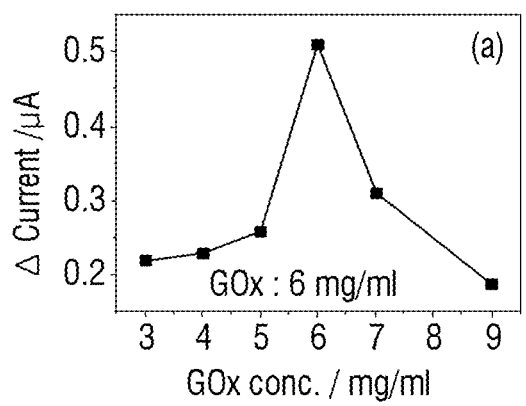
FIG. 10 is a graph showing experimental results of the optimization conditions for forming a polymer-enzyme electrode, specifically, optimization conditions for GOx concentration (a), TTCA concentration (b), the number of scans for polymerization (c), scanning speed (d), and glucose detection potential (e)
Figure 10:
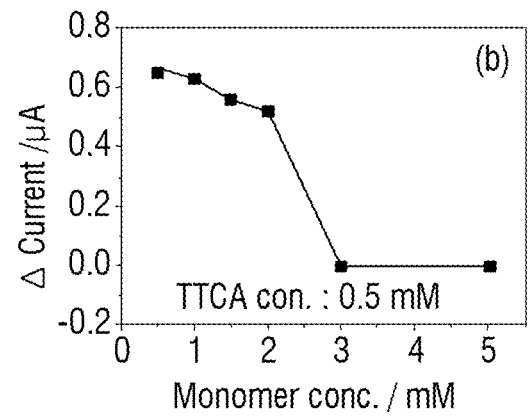
Figure 10:
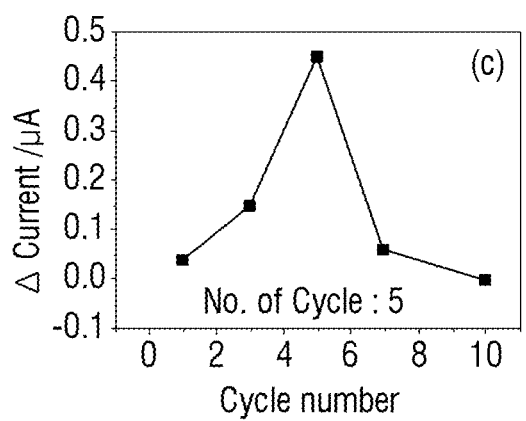
Figure 10:
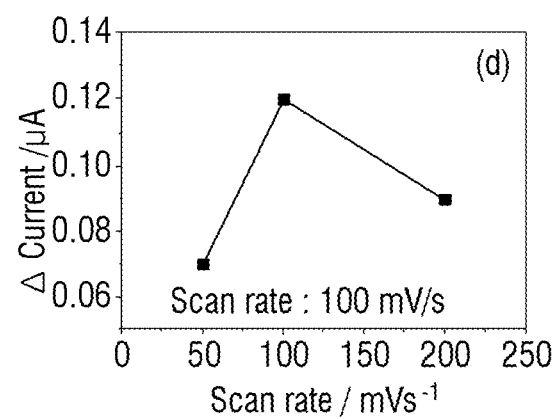
Figure 10:
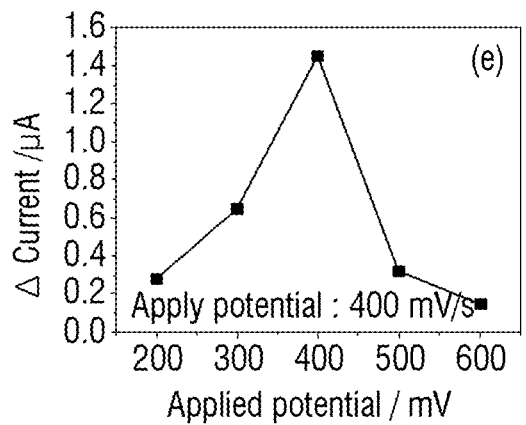

Graph (a) of FIG. 10 is an optimization experiment for GOx concentration in the preparation of a mixed solution of a monomer (TTCA) and an enzyme (GOx), wherein mixed solutions are generated by changing only the GOx concentration to 3, 4, 5, 6, 7, 9 mg/mL to create respective glucose sensors and measure glucose. Referring to graph (a) of FIG. 10, the oxidation current of the glucose increases until the GOx concentration is 3 to 6 mg/mL, and then the oxidation current decreases at the subsequent concentration. Therefore, the concentration of GOx is optimized to 6 mg/mL.

Graph (b) of FIG. 10 is an optimization experiment for the TTCA concentration at the time of preparing a mixed solution of a monomer (TTCA) and an enzyme (GOx). When the concentration of TTCA is 0.5 mM or more, the oxidation current of glucose may be reduced. Thus, the concentration of TTCA in the preparation of a mixture solution of the monomer and enzyme is optimized to 5 mM.

Graphs (c) and (d) of FIG. 10 show optimization experiments of the number of times of scanning and the scanning speed of the TTCA-GOx monomer at the time of electrophoretic polymerization by the cyclic voltammetry. The number of times of scanning and the scanning speed in the electrophoretic polymerization are important factors affecting the thickness of pTTCA-GOx and thus have a large influence on the glucose sensitivity. As a result, the maximum glucose oxidation current value is shown by the blood glucose sensor manufactured with five times of scanning (see (c) of FIG. 10) and at the scanning speed of 100 mV/s (see (d) of FIG. 10).

Graph (e) of FIG. 10 shows an optimization experiment for the potential for glucose detection using the time-current method. The detection voltage range is 200 to 600 mV. The oxidation current increased to 400 mV and then decreased from 500 mV. Therefore, the detection voltage of glucose using time-current method is optimized to 400 mV.

Figure 11:
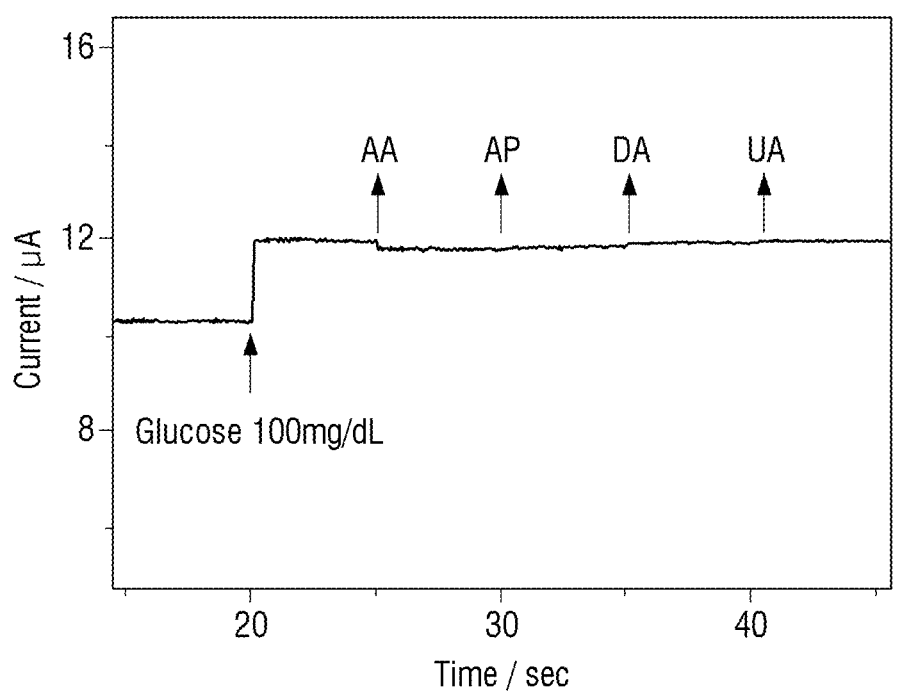
FIG. 11 is a view to explain an interference effect on ascorbic acid (AA), Acetaminophen (AP), Dopamine (DA), and Uric acid (UA) during the operation of a sensor reformed by AuZnOx/pTTCA-GOx/Nafion.

<Experimental Example 3> Evaluation of the Effect of Interfering Substances in Glucose Measurement FIG. 11 shows the results of measurement of glucose oxidation current when ascorbic acid (AA, 100 μM), Acetaminophen (AP, 100 μM), Dopamine (DA, 100 μM) and Uric acid (UA 100 μM) interfering substances are present. Specifically, using a microarray needle sensor including an electrode having a polymer structure layer/nepion coating layer (AuZnOx/pTTCA-GOx/Nafion) in which a Gox is covalently bonded to a gold-zinc oxide layer/pTTCA, signal changes in glucose is observed when the substances are present. In the case of AP, a decrease in glucose sensitivity is observed by about 11%, and in the remaining AA, DA, and UA, it is less than 5%, and it did not significantly affect the glucose detection signal.

Generally, in the case of a glucose sensor based on a gold electrode, various anions may be easily adsorbed on the gold electrode. In particular, Cl— ions may be strongly adsorbed on the surface of gold, inhibiting the oxidation reaction of glucose and hydrogen peroxide generated by the enzyme reaction. Therefore, by forming a metal alloy oxide (AuZnOx) layer, the amount of Cl— ion adsorbed on the metal surface is reduced and the sensitivity of glucose is improved. Therefore, the effect of Cl— ion is evaluated using the AuZnOx deposited glucose sensor. The sensitivity of glucose with or without Cl— ion (0.1 M) to 0.1 M PBS (pH 7.4) solution using a multi-metal alloy (AuZn) and a multi-metal alloy oxide (AuZnOx) layer is shown in table 1 below.

TABLE 1

|  | Without 0.1M saline | | With 0.1M saline | |
| --- | --- | --- | --- | --- |
|  | AuZn | AuZnOx | AuZn | AuZnOx |
| Sensitivity (μA/mM) | 1.16 | 1.23 | 0.11 | 0.43 |

Au-based sensors in the presence of Cl— ion may have low reactivity to glucose. Multi-metal alloy (AuZn)-based sensors and multi-metal alloy oxide (AuZnOx)-based sensors may have reduced sensitivity to glucose by 10.5 and 2.7 times, respectively. That is, it is observed that the sensitivity of the metal alloy to the glucose when the oxide (AuZnOx) layer is formed is much smaller. This means that by forming an oxide layer on the multi-metal alloy, Cl— ions may prevent adsorption on the metal surface, thereby preventing sensitivity deterioration to glucose. As a result, it is found that the glucose sensitivity of the AuZnOx-based sensor in the solution containing Cl— ion is 4 times higher than that of the AuZn-based sensor.

<Experimental Example 4> Glucose Detection Using Time-Current Method

Figure 12:
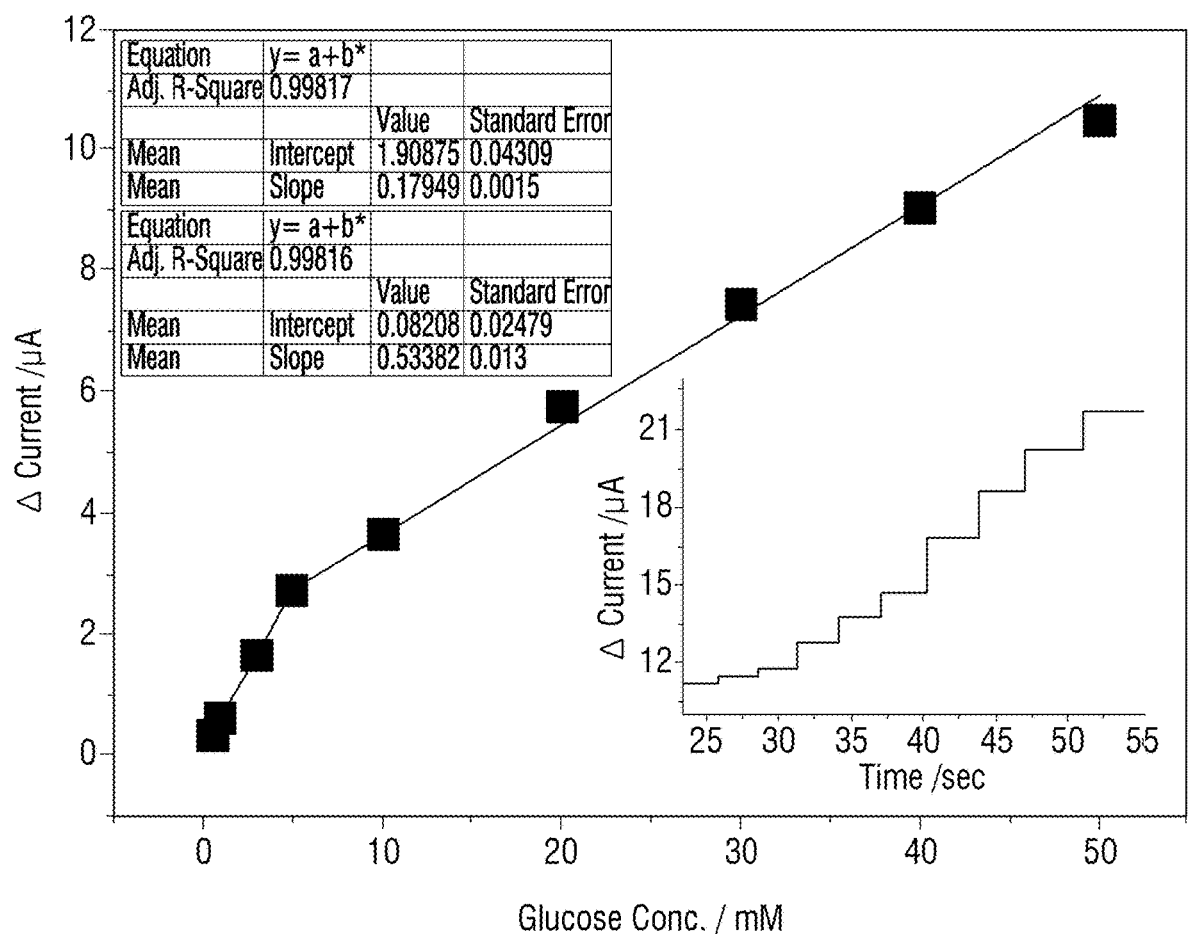
FIG. 12 is a graph showing a calibration curve according to glucose concentration at the time of operation of a sensor reformed by AuZnOx/pTTCA-GOx/Nafion.

FIG. 12 is a calibration curve for measuring glucose concentration by a time-zone current method using a microarray needle sensor based on Au/AuZnOx/pTTCA-GOx. FIG. 12 shows the results of measurement with three microneedle array sensors in a glucose concentration range of 100 μM to 50 mM. Two calibration curves are obtained at a low concentration range (100 μM to 5 mM) and a high concentration range (5 to 50 mM) with a detection limit of 92 μM. Correlation between calibration curves at low and high concentration ranges may be $I(\mu A)=(1.909\pm0.043)+(0.180\pm0.002)[C]$ (mM) and $I(\mu A)=(0.082\pm0.025)+(0.534\pm0.013)[C]$ (mM), and the correlation coefficient of the two relations may be 0.99. The average current value, the absolute standard deviation, and the coefficient of variation (percentage of the absolute standard deviation with respect to the average current value) of the glucose concentration range are shown in Table 2 below.

TABLE 2

| | Glucose concentration (mM) | | | | | | | |
| --- | --- | --- | --- | --- | --- | --- | --- | --- |
| | 0.5 | 1 | 5 | 10 | 20 | 30 | 40 | 50 |
| Average current value | 0.31 | 0.65 | 2.78 | 3.69 | 5.59 | 7.54 | 9.17 | 10.76 |
| Absolute standard deviation | 0.04 | 0.05 | 0.07 | 0.07 | 0.06 | 0.06 | 0.2 | 0.21 |
| Coefficient of variation | 13.2 | 7.3 | 2.4 | 1.9 | 1.0 | 0.73 | 2.18 | 1.93 |

Figure 13A:
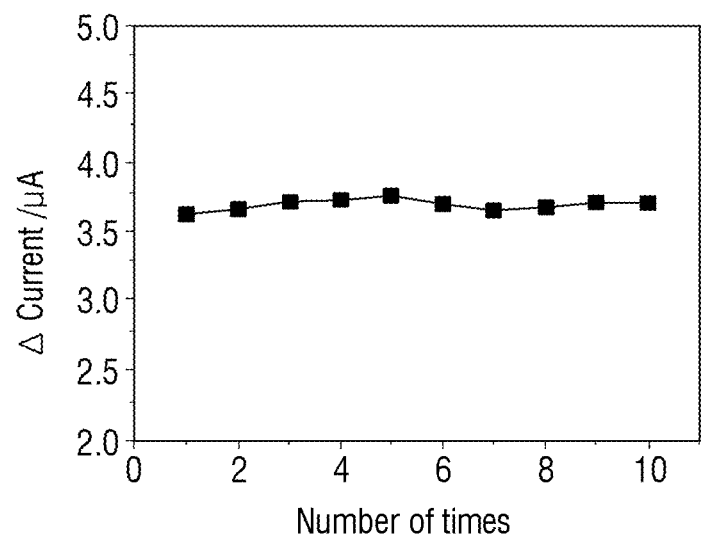
FIG. 13A is a graph showing reproducibility of a sensor by measuring a plurality of times using a biosensor according to an embodiment of the present disclosure.
Figure 13B:
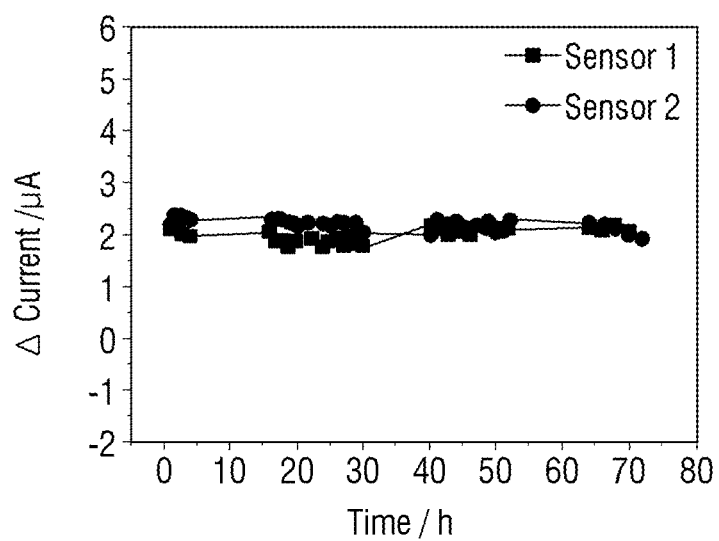
FIG. 13B is a graph showing stability by measuring glucose continuously for 3 (three) days using the biosensor according to an embodiment of the present disclosure.

<Experimental Example 5> Evaluation of Reproducibility for Glucose Measurement Glucose detection stability and reproducibility of the SUS/Au/AuZnOx/pTTCA-GOx sensor are tested. FIG. 13A shows the result of monitoring the change in sensitivity of glucose when measured by the same sensor 10 times. At this time, the concentration of glucose may be 10 mM. As a result of 10 measurements, the average current value and the coefficient of variation are 3.69±0.07 µA and 1.9%, respectively, which exhibit excellent repeated measuring stability. FIG. 13B shows the result of measuring the time when the sensor is soaked in PBS (pH 7.4)/0.1 M NaCl solution containing 10 mM glucose for 3 days. Referring to FIG. 13, for 3 (three) days, the sensitivity of glucose may not be significantly affected to obtain the stable result. In other words, the glucose sensor based on the micro array needle according to an embodiment of the present disclosure may be attached to the skin with minimal invasion and used as a sensor for continuously detecting glucose from body fluids.

Although exemplary embodiments have been shown and described, it will be appreciated by those skilled in the art that changes may be made to these exemplary embodiments without departing from the principles and spirit of the present disclosure. Accordingly, the scope of the present disclosure is not construed as being limited to the described exemplary embodiments, but is defined by the appended claims as well as equivalents thereto.

What is claimed is:

1. A method for manufacturing a biosensor, the method comprising:
    generating monomers formed by covalent boding between 5,2':5',2''-terthiophene-3'-carboxylic acid (TTCA) and an enzyme; and
    polymerizing the monomers on an electrode and depositing a polymer layer on the electrode.

2. The method as claimed in claim 1,
    wherein the enzyme comprises an amine group, and
    wherein the generating of the monomers comprises:
        using 1-Ethyl-3-[3-(dimethylamino)propyl]carbodiimide hydrochloride (EDC) and N-hydroxysuccinimide (NHS); and
        activating a carboxyl group of the TTCA to form covalent bonding between the carboxyl group of the TTCA and the amine group of the enzyme.

3. The method as claimed in claim 1, wherein the enzyme is selected from a group consisting of glucose oxidase, glucose dehydrogenase, hexokinase, glutamic oxaloacetic transaminase, and glutamine pyruvic transaminase.

4. The method as claimed in claim 1,
    wherein the depositing of the polymer layer on the electrode comprises:
        immersing the electrode in a solution containing the monomers; and
        applying a voltage to the electrode to polymerize the monomers on the electrode by electropolymerization.

5. The method as claimed in claim 1, further comprising:
    coating an electrode surface with a gold-zinc alloy oxide layer (AuZn oxide layer),
    wherein the depositing of the polymer layer on the electrode comprises:
        polymerizing the monomers on an electrode coated with the gold-zinc alloy oxide layer.

* * * * *